United States Patent [19]

Ichihara

[11] Patent Number: 4,639,599

[45] Date of Patent: Jan. 27, 1987

[54] RING TYPE SINGLE-PHOTON EMISSION CT IMAGING APPARATUS

[75] Inventor: Takashi Ichihara, Ootawara, Japan

[73] Assignee: Kabushiki Kaisha Toshiba, Kawasaki, Japan

[21] Appl. No.: 732,078

[22] Filed: May 9, 1985

[30] Foreign Application Priority Data

May 10, 1984 [JP] Japan ................................. 59-94797
May 10, 1984 [JP] Japan ................................. 59-94798

[51] Int. Cl.$^4$ ............................................. G01T 1/164
[52] U.S. Cl. ................................ 250/363 S; 250/369; 250/370
[58] Field of Search ............... 250/363 SB, 366, 370 I, 250/370 H, 370 G, 363 SR, 369, 363 SC; 378/10

[56] References Cited

U.S. PATENT DOCUMENTS

4,389,569 6/1983 Hattori et al. ................. 250/363 SB
4,511,799 4/1985 Bjorkholm ................. 250/370 G X

*Primary Examiner*—Carolyn E. Fields

*Attorney, Agent, or Firm*—Finnegan, Henderson, Farabow, Garrett & Dunner

[57] ABSTRACT

In a single-photon emission computerized tomography imaging apparatus, an inner ring member and an outer ring member are concentrically arranged with respect to an object under examination to which radioisotope has been administered. A plurality of detector elements such as the germanium semiconductor are mounted on the inner ring member. A plurality of detector elements such as the sodium iodide scintillator and the photomultiplier are mounted on the second ring member. First and second analyzers having a plurality of single channel analyzers are connected to receive first and second detector signals from the inner and outer detector elements. The first and second analyzers analyze data on the positional information of the inner and outer detector elements and data on the energy information of the gamma ray photon incident upon the inner and outer detector elements. Based upon two sets of data, an image reconstruction unit reconstructs a tomographic image of the object under examination.

20 Claims, 6 Drawing Figures

RING TYPE SINGLE-PHOTON EMISSION CT IMAGING APPARATUS

BACKGROUND OF THE INVENTION

I. Field of the Invention

The present invention relates to an emission computerized tomograph imaging apparatus, and more particularly to a ring type single-photon emission CT imaging apparatus which detects radiation, e.g., gamma ray photons of radioisotope that has been injected into an object under examination such as a patient, so as to process detection signals, thereby obtaining a CT image from a three-dimensional distribution of radioactivity of radioisotope within the object.

II. Description of Prior Art

In general, emission computerized tomography commonly referred to as "ECT" is known from, e.g., U.S. Pat. No. 4,289,965 to Koga et al. issued on Sept. 15, 1981 and U.S. Pat. No. 4,389,569 to Hattori et al. issued on June 21, 1983. ECT is a technique for obtaining an image of the distribution (i.e., spatial position) of radioactivity of radioisotope in a desirable slice normal to the longitudinal axis of a body of a patient within a region of interest thereof by administering to the patient a pharmaceutical compound labelled with the radioisotope, for detecting from outside of the body the gamma radiation emitted by the isotope that has been accumulated in the above region of interest, and for processing the detection signals by a computer to obtain the tomographic image.

In such a known ECT, a plurality of radiation detectors are circumferentially arranged about the longitudinal axis of a body, and directed to the body at different angles within 360 degrees in a given slice of a body so as to detect the radioactivity of radioisotope. Generally, a collimator made of the radioactivity protection material, e.g., lead is positioned in front of the respective detectors so as to selectively receive gamma rays having a predetermined travel direction and a given energy level.

In this system, the sensitivity and resolution of the detector system are influenced to a greater extent by the employed collimators. That is, since the energy level of gamma rays that have commonly been employed in the field of nuclear medicine is rather high, say from tens to hundreds KeV (Kilo-electron volts), a thickness of the collimator's wall must be thick, resulting in the insensitivity and lowered resolution of the detector system.

In the above-described ECT having a plurality of detectors which are positioned in a ring shape around the patient (referred to as "ring type ECT"), especially a single-photon mode ECT, it is required to employ collimators that can selectively receive the gamma rays in the specific directions only. This type of the collimator is known as a parallel hole collimator and a fin shape collimator. As previously described, the employment of such collimators causes resolution and sensitivity to deteriorate. Moreover, such a ring type single-photon ECT is not available to perform the dynamic scanning by which movements of the radioisotope within a body under examination can be measured.

It is therefore an object of the present invention to provide a ring type single-photon ECT imaging apparatus in which electronic collimators, instead of mechanical collimators, are employed to realize the dynamic scanning.

A further object of the present invention is to provide a compact ECT imaging apparatus for counting gamma rays with higher accuracy.

SUMMARY OF THE INVENTION

The object of the present invention may be accomplished by providing a ring type single-photon ECT imaging apparatus comprising:

a first ring-shaped member including thereon a plurality of first detector elements and surrounding an object under examination to which radioisotope has been administered;

a second ring-shaped member including thereon a plurality of second detector elements and concentrically surrounding the first ring-shaped member, whereby a gamma ray irradiated from the administered radioisotope through the object firstly scatters in one of the first detector elements, thereby producing a first detector signal and thereafter the scattered gamma ray disappears in one of the second detector elements, thereby producing a second detector signal;

a first analyzing unit including a plurality of first single channel analyzers coupled to the corresponding first detector elements for analyzing whether an energy level of the first detector signal is involved in a first predetermined level width of the first single channel analyzers, thereby producing a first analyzing signal;

a second analyzing unit including a plurality of second single channel analyzers coupled to the corresponding second detector elements for analyzing whether an energy level of the second detector signal is involved in a second predetermined level width of the second single channel analyzers, thereby producing a second analyzing signal;

an image reconstruction unit for reconstructing a computerized tomographic image signal by processing the first and second analyzing signals, said first and second analyzing signals containing both first data on the positional information of the first and second detector elements upon which said gamma ray and scattered gamma ray are incident, and second data on the energy information derived from the first and second analyzing units; and, a monitor for displaying a computerized tomographic image by receiving the reconstructed tomographic image signal.

BRIEF DESCRIPTION OF DRAWINGS

For a better understanding of the object of the present invention, reference is made to the following detailed description of the invention to be read in conjunction with the following drawings, in which.

DETAILED DESCRIPTION OF THE PREFERRED EMBODIMENTS

Before describing various embodiments according to the present invention, the principle of measurement of gamma rays incident on detectors will now be summarized.

Figure 1:
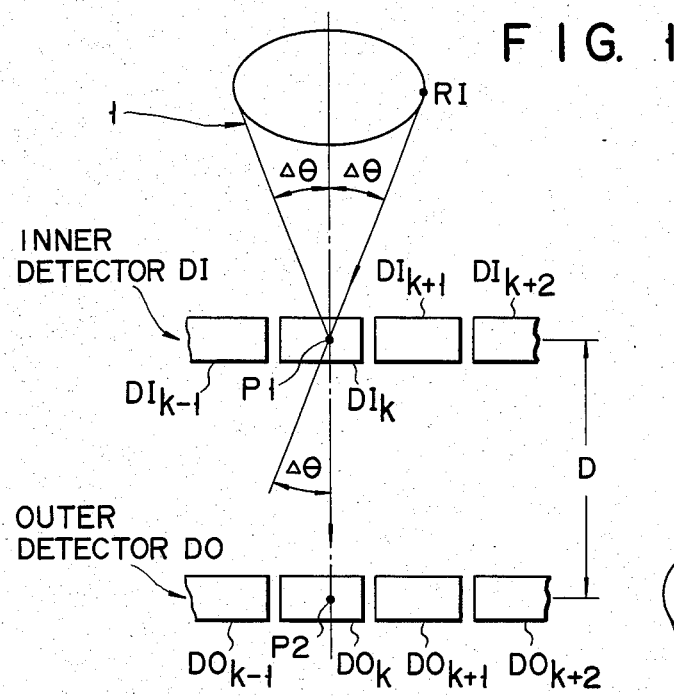
FIGS. 1 to 3 are graphical illustrations for explaining the basic idea according to the present invention.
Figure 2:
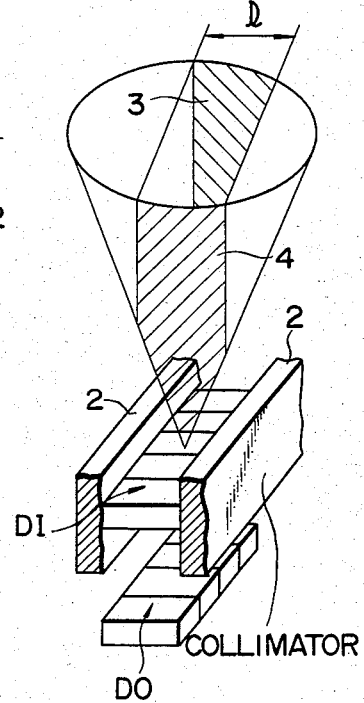
Figure 3:
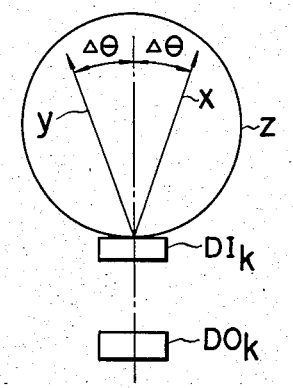

FIGS. 1 to 3 illustrate trails of a gamma ray of radioisotope (referred to as "RI") positioned in a certain point. A plurality of detector elements $DI_N$ (N=1~n) are arranged along a circle, which constitute an inner detector group DI having a ring shape. Furthermore, a plurality of detector elements $DO_N$ (N=1~n) are arranged along another circle, which constitute an outer detector group DO having another ring shape. Both these inner and outer detector groups constitute a detector unit. The inner detector group faces an object under examination (not shown in detail) from which radioactivity (gamma ray) irradiates omnidirectly. The gamma ray irradiated from RI which is positioned at a certain position within the object is incident upon one detector element $DI_k$ of the inner detector group DI. It scatters within this detector element $DI_k$ and thereafter disappears in one detector element $DO_1$ of the outer detector group DO. The scattering angle of the gamma ray in the inner detector element $DI_k$ is denoted as "$\Delta\theta$". The gamma ray originally has an energy level of "E". After scattered in the inner detector element $DI_k$, the energy of the gamma ray is reduced to E ($\Delta E = E - E'$).

The detection signal of this inner detector element $DI_k$ is represented by the following equation (1), which is obtained from the relationship between the scattering angle $\theta$ of Compton effects and the energy shift of the incident gamma ray:

$$E' = \frac{E}{1 + 1.96E(1 - \cos \Delta\theta)} \quad (1)$$

Where the detection signals (energy levels) E and E' are represented in MeV (Mega-Electron Volt).

Based upon this detection signal, the energy loss $\Delta E$ caused by the scattering effects can be measured and the reduced energy E' can also be measured by the outer detector element $DO_k$.

When the condition of $E = E' + \Delta E$ is satisfied and further the gamma ray is continuously detected in the inner and outer detector elements $DI_k$ and $DO_k$, recognition can be made that the above-described scattering and absorption phenomena occur, so that the positions of both inner and outer detector elements $DI_k$ and $DO_k$ can be correctly detected.

Furthermore, the scattering angle $\Delta\theta$ can be obtained from equation (1) based upon the energy levels E and E'.

From the collected data, i.e., the positions of the inner and outer detector elements $DI_k$ and $DO_k$ and the scattering angle $\Delta\theta$, it can be judged that the trail of the incident gamma ray exists anywhere in all surfaces of a circular cone 1. The circular cone 1 has its central axis intersecting the scattering point P1 of the inner detector element $DI_k$ and the scattering point P2 of the outer detector element $DO_k$, and has the vertical angle $2\Delta\theta$.

Introduction of a collimator 2 for determining the slice width 1 as shown in FIG. 2 into the inner detector group DI enables the trails of the incident gamma rays to be traced. These gamma rays may exist in the hatched portions 3 and 4 as shown in FIG. 2.

This implies that the trails of the gamma rays are possibly present in two directions indicated by x and y, and it is also possible to realize the back projection in the x and y direction by acquiring and processing the data as much as possible.

In such a case, the scattering angle $\Delta\theta$ of the gamma ray to be acquired can be freely set by properly presetting, for example, the energy selection (capture) width (referred to as "energy level width") of the inner detector group DI and that of the outer detector group DO within a given range. This range is defined by the following equation; $E = E' + \Delta E$.

Also, all of the gamma rays having various scattering angles $\Delta\theta$ can be detected. Moreover, the maximum resolution can be realized by selecting the energy level width to be able to capture the gamma rays under the condition that errors in the measurement can be minimized. In this condition, the sensitivity is sacrificed for resolution to some degree.

If the radius of the inner ring for the inner detector elements DIn is, for instance, decreased and thus a distance "D" between the inner and outer detector elements is increased, an improvement can be obtained in the detection sensitivity.

Various kinds of the mechanism for changing the radius of the ring member can be employed. For example, such a mechanism is known in that the grooves on which each of the detector elements is slidable in the radial direction of the ring member are formed in a supporting member for supporting the inner detector group DI, and all of the inner and outer detector elements can be simultaneously slid in the radial direction by means of the lead screws and gears. This mechanism is disclosed, e.g., in U.S. Pat. No. 4,181,939 to Lyonos.

When the known mechanism is employed, a length of one pixel in the reconstructed images which can give a great influence to spatial resolution, can be preset to be as short as possible. This short preset is realized in the following cases. One portion of an object such as head can be scanned even if the radius of the inner ring is small, and the other portion of the object such as abdomen cannot be scanned unless the radius of the inner ring is large. This advantage is enhanced particularly in the limited capacity for the measuring system and data processing system.

It should be noted that the following definition is made in the present specification. An energy level of a single channel analyzer implies a width or tolerance for capturing an incident gamma ray. A pulse height or peak value corresponds to an energy level.

Figure 4:
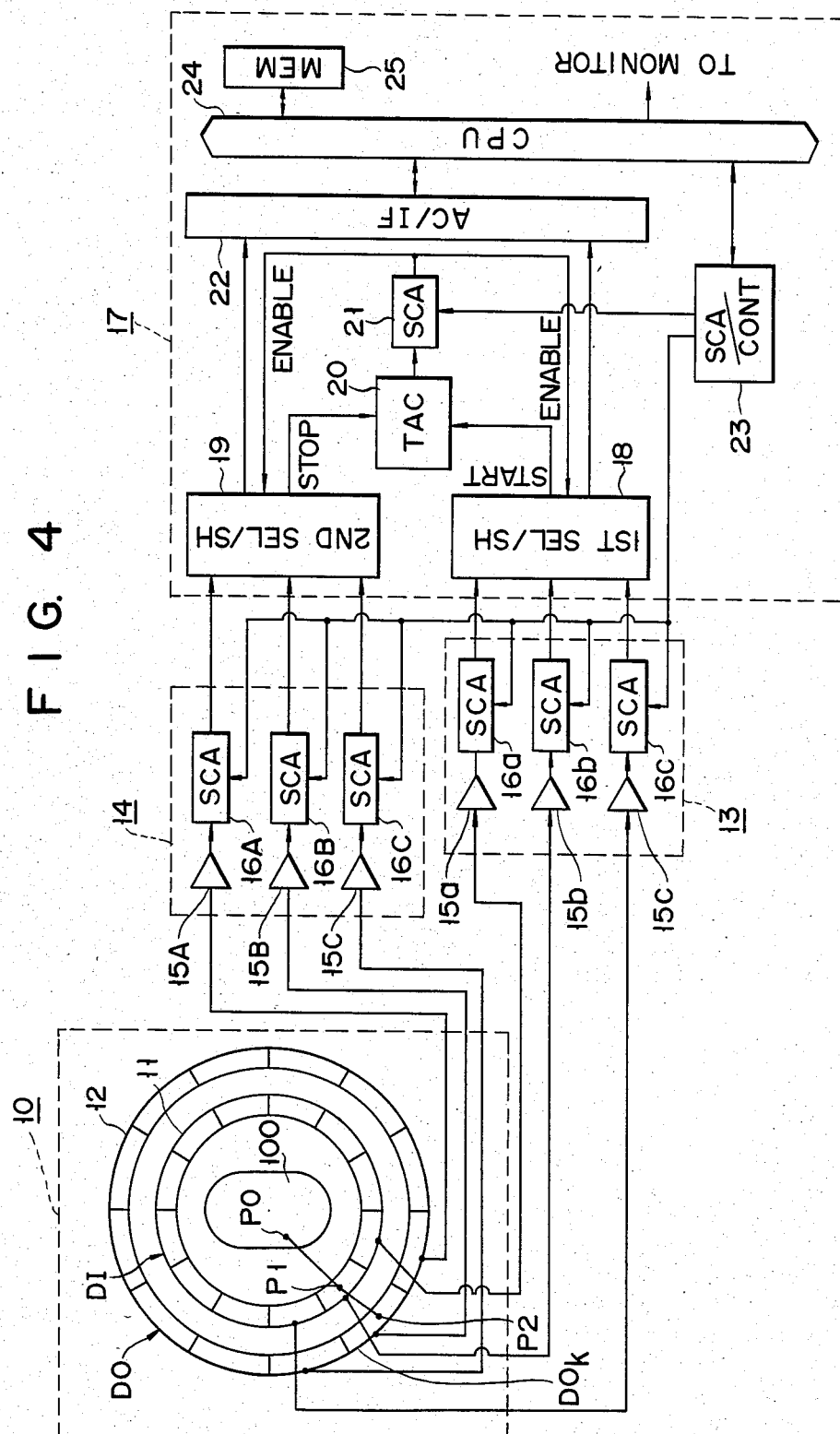
FIG. 4 is a schematic diagram of a ring type single-photon ECT imaging apparatus according to a first preferred embodiment.

Referring to FIG. 4, a ring type single-photon emission ECT imaging apparatus as a first embodiment will now be described, into which the above-mentioned principle of the gamma ray measurement has been introduced.

A gantry 10 is constructed by the inner detector group DI and the outer detector group DO. These detector groups are mounted on the respective inner and outer rings 11 and 12. A proper mechanical member (not shown) is coupled to the inner and outer rings 11 and 12. The inner ring 11 is movable in a radial direction, so that its radius, or the distance D between both rings 11 and 12 can be changed. Since such a mechanical member for the ring movement is known from, e.g., U.S. Pat. No. 4,181,939, no further explanation is made.

The inner detector elements $DI_N$ are made of a combination with, e.g., an NaI(sodium iodide) scintillator and a photomultiplier. The outer detector elements $DO_N$ are made of e.g., a very pure Ge (germanium) semiconductor.

A first analyzer unit 13 is connected to the inner detector group DI, and a second analyzer unit 14 is connected to the outer detector group DO.

In these analyzer units 13 and 14, a plurality of series circuit arrangements are provided. The number of the series circuit arrangement corresponds to that of the inner and outer detector elements $DI_N$ and $DO_N$. The series circuit arrangement is constructed by a preamplifier 15 and a single channel analyzer 16. For example, the inner detector element $DI_k$ is connected to the preamplifier 15b and the single channel analyzer 16c of the first analyzer unit 13.

For convenience and clarity of illustration, each of these analyzer units 13 and 14 has only three channels of single channel analyzers 16a to 16c and 16A to 16C, respectively.

Outputs of the first and second analyzer units 13 and 14 are supplied to an image reconstruction unit 17. Precisely speaking, these outputs are delivered to first and second selector/sample holders 18 and 19. The image reconstruction unit 17 is constructed by the first and second selector/sample holders 18, 19, a time-to-amplitude converter 20, a single channel analyzer 21, an acquisition interface 22, a controller for single channel analyzer 23, a central processing unit (CPU) 24, and a memory 25.

Outputs of this image reconstruction unit 17 are to be supplied to a monitor (not shown).

Upon receipt of the outputs of the first and second selector/sample holders 18 and 19, the time-to-amplitude converter 20 controls its start and stop operations. The following single channel analyzer 21 analyzes a pulse having a given pulse height (peak value) which is applied from the converter 20. The acquisition interface 22 acquires from the output of the single channel analyzer 21 the detection position information and energy information. The acquisition interface 22 acquires both information on detection positions and emission energy from the outputs of the first and second selector/sample holders 18 and 19 based upon the output of the single channel analyzer 21. The SCA controller 23 controls the energy levels (crest value, or peak value) and the energy level width of the single channel analyzers 16A to 16C and 16a to 16c of the first and second analyzer units 13 and 14. As is known, the central processing unit 24 controls the acquisition interface 22 and the SCA controller 23 and also temporarily stores the outputs of the first and second selector/sample holders 18 and 19, which are thereafter stored in the memory 25.

With reference to FIGS. 1 through 4, operation of the ring type single-photon ECT imaging apparatus will now be described.

As an initial condition, the object under examination 100 has been administrated material tagged with radionuclides such as $TC^{99m}$ (technetium). This material administration is known as IN VIVO method. This radioisotope irradiates a single gamma ray photon. The gamma ray is first incident upon a certain element of the inner detector group DI(assuming the inner detector element "$DI_k$" in this embodiment). In this inner detector element $DI_k$, the incident gamma ray scatters under the condition that the scattering angle is $\theta$ and the lost energy (level) during the scattering is $\Delta E$. Then the scattered gamma ray is again incident upon a certain element of the outer detector group DO (assuming the outer detector element "$DO_k$" in this embodiment). In this outer detector element $DO_k$, the photoelectric effect occurs so that the scattered gamma ray is detected.

It should be noted that since the energy level "E" of the gamma ray incident upon the inner detector element $DI_k$ is already known, the energy level (peak value) of the respective single channel analyzers 16a, 16b, 16c of the first analyzer unit 13 and the energy level width thereof can be preset via CPU24 by the SCA controller 23, and, on the other hand, similarly the energy level (peak value) of the respective single channel analyzers 16A, 16B, 16C of the second analyzer unit 14 and the energy level width thereof can be preset through CPU 24 by the same controller 23. That is, the first-mentioned energy level is $\Delta E$, and the last-mentioned energy level is $E'$(i.e., $E - \Delta E$).

The gamma ray irradiated from a point Po within the object 100, the energy level of which is "E", is incident upon the inner detector element $DI_k$ and scatters therein at a scattering point $P_1$. The scattered gamma ray is incident on an incident point $P_2$ of the outer detector element $DO_k$ and completely disappears therein.

The output of the inner detector element $DI_k$ is fed to the first analyzer unit 13 in which it is amplified to a given signal level by the preamplifier 15b and the amplified output is supplied to the single channel analyzer 16c. The single channel analyzer 16c can recognize that the incident gamma ray exists within a predetermined energy level and therefore delivers a pulse having a given peak value (corresponding to the lost energy level $\Delta E$) to the first selector/sample holder 18.

Upon receipt of the pulse of the single channel analyzer 16b, the first selector/sample holder 18 sampling-holds the position (location) of the inner detector element, i.e., DIk and the peak value (i.e., pulse height), and simultaneously permits the time-to-amplitude converter 20 to start its counting operation.

On the other hand, the output of the outer detector group DO is supplied to the second analyzer unit 14, i.e., the preamplifier 15B and the single channel analyzer 16B. The single channel analyzer 16B can recognize that the incident scattered gamma ray exists within a preset energy level $(E - \Delta E)$ and thus delivers a pulse having a given peak value, i.e., a pulse height corresponding to the energy level $(E - \Delta E)$ to the second selector/sample holder 19. Receiving this pulse from the single channel analyzer 16C, the second selector/sample holder 19 sampling-holds the position (location) of the outer detector element $DO_k$ and also enables the counting operation of the time-to-amplitude converter 20 to be stopped.

After it is stopped, the time-to-amplitude converter 20 delivers to the single channel analyzer 21 a single pulse having a pulse height corresponding to the time lapse between the start and stop of the counting operation.

Then the single channel analyzer 21 delivers to the first and second selector/sample holders 18 and 19 an enable signal, when the above single pulse corresponds to the time lapse during which the counting operations have been substantially simultaneously effected by both the inner and outer detector elements $DI_k$ and $DO_k$. This time lapse is predetermined by the SCA controller 23.

Upon receipt of the enable signal of the single channel analyzer 21 in the image reconstruction unit 17, the first and second selector/sample holders 18 and 19 can deliver data on the energy information and the detection position information which has been previously held, to the acquisition interface 22. The energy information data includes the energy level $\Delta E$ which has been lost during the scattering phenomenon. The data on the detection position includes the locations of the inner and outer detector elements $DI_k$ and $DO_k$.

Thus the acquired data is, for example, stored in the memory 25 by means of the direct memory access (DMA).

Such a data set is carried out for the whole body of the patient (object). That is, the energy measurement based upon equation (1) is performed with respect to one slice of the body at 360 degrees. After the entire energy measurement is completed, the computerized tomographic image of the radioisotope distributions can be reconstructed under the control of CPU 24.

The basic operation of the first embodiment will now be summarized.

When the gamma ray having its energy level of E is incident upon the inner detector group, scattering phenomenon occurs and the energy level of $\Delta E$ is lost therein. Just after an occurrence of this scattering phenomenon, the outer detector group receives the scattered gamma ray having the energy level of (E—$\Delta E=E'$) from the inner detector group. When the scattered gamma ray completely disappears in the outer detector group due to photoelectric effects, so that the energy level of E' smaller than E is detected therefrom. If there exists coincidence between the original energy level E and the sum of the lost energy $\Delta E$ and the expired energy E', the simultaneous counting operation is effected in the inner and outer detector groups. As previously described, these energy levels $\Delta E$ and E' have been determined by presetting the energy levels of the corresponding single channel analyzers in the first and second analyzer units 13 and 14. In other words, the radiation counting operation by the time-to-amplitude converter 20 can be correctly performed because the energy levels of the channel analyzers have been previously adjusted to a predetermined value in accordance with the sort of the available radioisotope.

In a practical case, the energy levels of the first and second single channel analyzers 16a to 16c and 16A to 16C have a certain variation range, i.e., first and second energy level widths, respectively and the energy level of the third single channel analyzer 21 also has a given variation range, i.e., a third energy level width. It should be noted that the first and second energy level widths are preset to be wider than the third energy level width.

Consequently, an improvement can be made in not only the counting efficiency for the gamma rays, but also the accurate detection. Moreover, since the time-to-amplitude converter 20 performs the coincidence counting, the incident gamma rays can be detected with higher accuracy.

Figure 5:
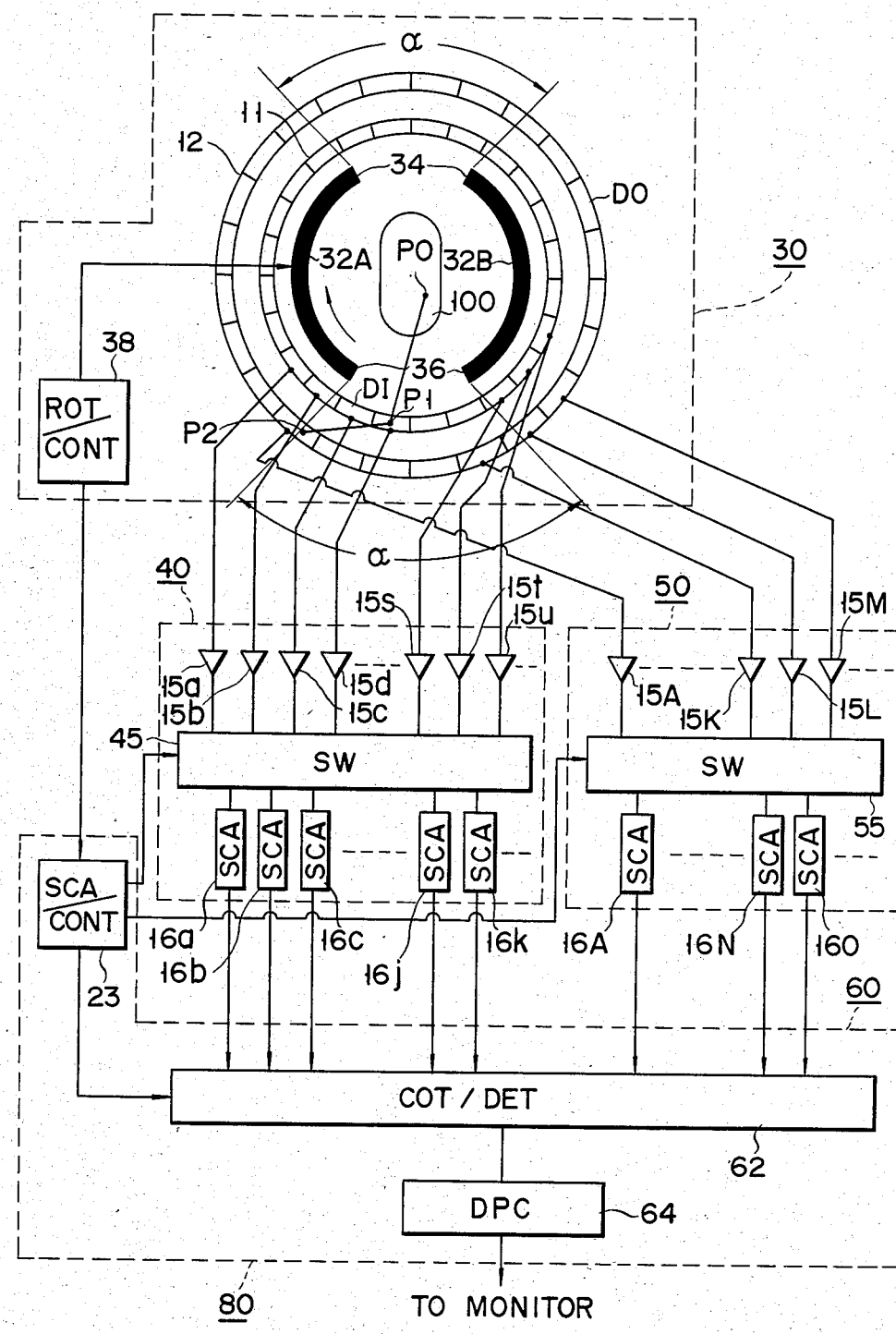
FIG. 5 is a schematic diagram of a ring type single-photon ECT imaging apparatus according to a second preferred embodiment.

Referring to FIG. 5, a description will be made of a ring type single-photon ECT imaging apparatus as a second embodiment.

It should be noted that the same or similar circuit elements in FIG. 5 are indicated by the same reference numerals as those in FIG. 4.

In FIG. 5, a gantry 30 is constructed by the inner and outer detector groups DI and DO which are mounted on the inner and outer rings 11 and 12 respectively, and further a pair of ring-shaped shield members 32A and 32B. The shield members 32A and 32B are spaced from the inner detector group DI at a given distance. Two openings 34 and 36 are formed by these shield members 32A and 32B. The shield members are mechanically rotated under the control of a rotation controller 38 around a center of the gantry 30 where the object under examination 100 is located. The rotation controller 38 enables the shield members 32A and 32B to be rotated at a high speed and produces data on positional information of the shield members, which is sent to the SCA controller 23 of the image reconstruction unit 80.

As seen from the opening configuration of the shield members 32A and 32B, the gamma ray irradiated from the original point Po within the object 100 is incident upon only a limited number of the inner detector elements $DI_N$. This number is determined by an angle $\alpha$(alpha) of the openings 34 and 36. This limitation can be also applied to the number of the outer detector elements $DO_N$. As a result, it is not necessary to employ the same number of the single channel analyzers 16a to 16l as that of the detector elements $DI_N$ or $DO_N$. That is to say, since there are located twelve inner detector elements 16a to 16l within the range defined by the opening's angle $\alpha$, the number of the single channel analyzers is 12. In contrast with the twelve single channel analyzers, it is necessary to employ the same number of the preamplifiers as those of the inner or outer detector elements.

Accordingly, only twelve detection signals are supplied to the respective single channel analyzers 16a to 16l or 16A to 16P by controlling the switching member 45 or 55 to conduct the outputs of the preamplifiers to the corresponding single channel analyzers. This switching control is performed by receiving the control signal derived from the SCA controller 23. The SCA controller 23 received data on the rotation information from the rotation controller 38. Thus, the switching operation is carried out in synchronism with rotation of the shield members 32A and 32B.

The image reconstruction unit 60 is constructed by a counting circuit for coincidence counting 62, a data processing circuit 64 and the above-described SCA controller 23. The counting circuit for coincidence counting 62 receives the outputs of the single channel analyzers 16a to 16n and 16A to 16N the first and second analyzer units 40 and 50. The output of the counting circuit for coincidence counting 62 is fed to the data processing circuit 64. The output (reconstructed image signal) of the data processing circuit 64 is supplied to the monitor (not shown). The SCA controller 23 controls the switching members 45 and 55 and the counting circuit for coincidence counting 62.

It is understood that the functions of the counting circuit for coincidence counting 62 and the data processing circuit 64 are practically identical to that of the image reconstruction unit 17 in the first preferred embodiment.

Operations of the second embodiment will now be described. The object 100 has been administerated radioisotope, whereby the gamma ray photons emit from the object 100. The gamma ray photons are allowed to be incident upon only the limited number of the inner detector elements $DI_N$ which are determined by the angle $\alpha$(alpha) of the openings 34 and 36.

In this case, since the shield members 32A and 32B are rotated about the object 100 at a high speed, the opening ranges defined by the angle $\alpha$ are also moved (rotated) along a circle path.

In accordance with the rotation of the shield members 32A and 32B, the data on the rotation (position) information is produced in the rotation controller 38 and transferred to the SCA controller 23. As a result, the SCA controller 23 controls the first and second switching members 45 and 55 so as to establish close circuits between the preamplifiers, for example, 15a to 15f and 15A to 15H and the corresponding single channel analyzers 16a to 16f and 16A to 16H. These preamplifiers are located within the range defined by the angle α of the openings 34 and 36.

Thus, the energy level of the gamma ray scattered in any one of the inner detector elements located within the above range, and the position of the inner detector element are detected in the first analyzer unit 45. Furthermore, the position of any one of the outer detector elements within the above range, in which the scattered gamma ray completely disappears, is detected in the second analyzer unit 55. The data on the energy information and also the detection information is counted by the detection circuit for coincidence counting 62.

It is understood that both the energy levels of the single channel analyzers in the first and second analyzer units 16 have been previously preset to a predetermined value the same as in the first preferred embodiment. The resultant data of the counting circuit 62 is processed in the data processing circuit 64 based upon the above-described principle measurement (equation) so as to determine the trail of the incident gamma ray. Such measurement and data processing are repeated for all slice directions (360 degrees around the object). From the resultant data acquired for all slice directions, a computerized tomographic image of the radioisotope distribution can be reconstructed in the data processing circuit 64. The reconstructed image signal is further supplied to the monitor so as to display a visual CT image.

According the second embodiment, since a pair of shield members 32A and 32B is employed inside the inner detector group DI, the gamma ray incident range with respect to the inner detector group is restricted to the angle α. Accordingly, the probability that the incident gamma ray scatters and disappears in the other detector elements is less than that within the above range, resulting in an improvement in spatial resolution because of a reduction in the chance coin- cidence.

Furthermore, the particular advantage is obtained in that since the inner and outer detector groups DI and DO are fixed with respect to the object 100 and the shield members are rotated around the object, it is not necessary to connect the signal cables to the rotation object (i.e., the detector groups) in cases where the detector groups are rotated around the object and also the shield members can be rotated at a high speed. In other words, it is also possible to realize a simple circuitry and a compact and inexpensive apparatus.

Figure 6:
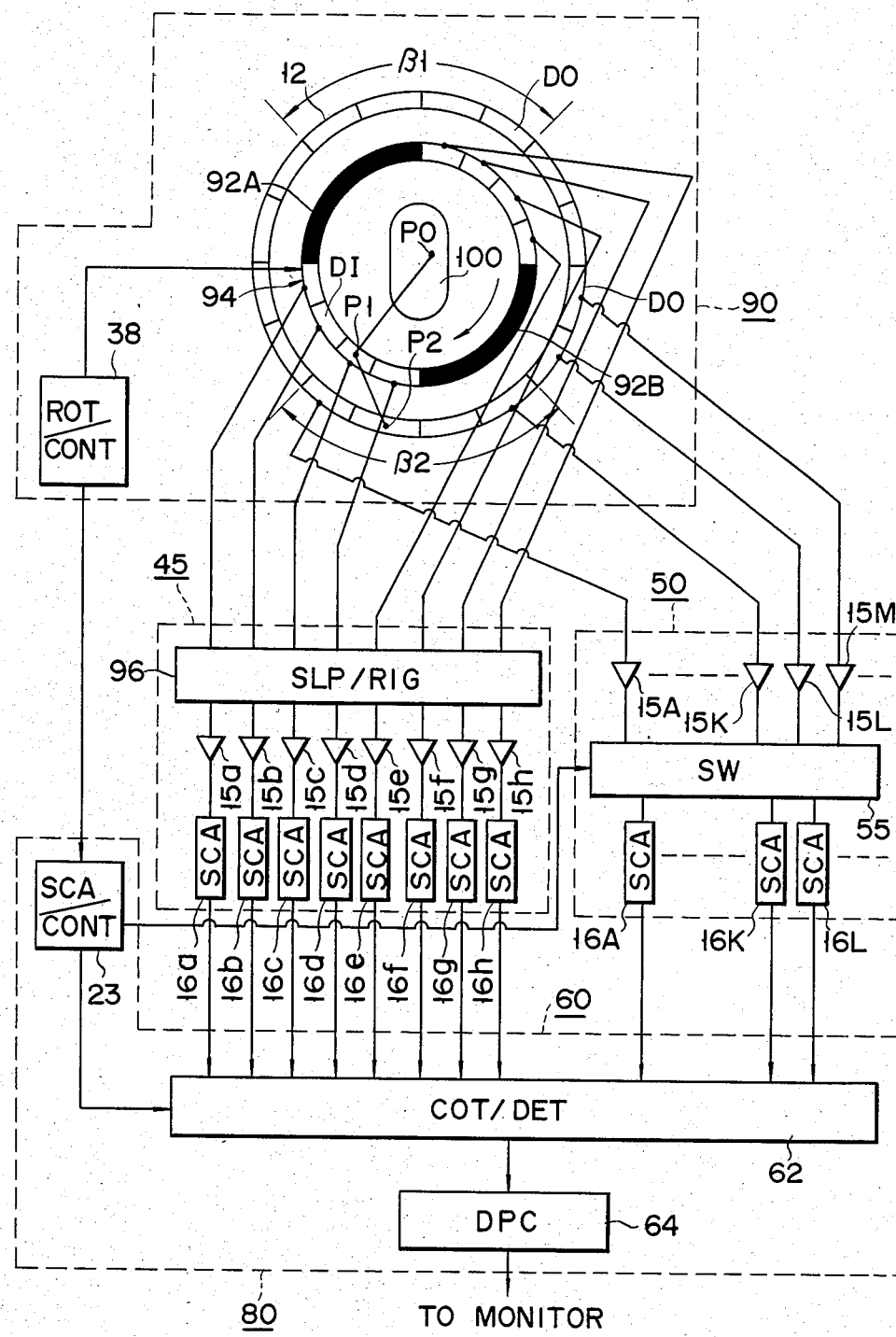
FIG. 6 is a schematic diagram of a ring type single-photon ECT imaging apparatus according a third preferred embodiment.

Referring to FIG. 6, a third preferred embodiment will now be described.

It should be noted that the same reference numerals shown in FIG. 5 will be employed as those for denoting the same circuit elements shown in FIG. 6.

A gantry 90 of a ring type single-photon ECT imaging apparatus is mainly constructed by the inner detector group DI and the outer detector group DO. The inner detector group DI includes on the inner ring 94 a smaller number of detector elements than in the previous preferred embodiments. For example, 8 (eight) elements DIa to DIh are mounted on the inner ring 94 as shown in FIG. 6. That is, a pair of radiation shield members 92A and 92B is sandwiched with a half of the eight detector elements DIa to DId and DIe to DIh.

Outside the inner detector group DI, the outer ring 12 on which a plurality of outer detector elements DO are mounted is concentrically positioned.

In this embodiment, the inner ring 94 is rotated by the rotation controller 38 in a direction indicated by an arrow at a high speed. Outputs of these inner detector elements DIa to DIh are supplied via the known slip ring mechanism 96 of the first analyzer unit 45 to the corresponding preamplifiers 15a to 15h and the corresponding single channel analyzers 16a to 16h.

While the inner ring 94 is rotated at a high speed, on which two detector elements DIa to DId members are alternately mounted, the detector signals are continually supplied to the corresponding preamplifiers and the single channel analyzers, the energy levels of which have been preset.

The outer ring 12 on which a plurality of outer detector elements are mounted is fixed with respect to the inner ring 11. The switching member 55 interposed between the preamplifiers 15A to 15N and the single channel analyzers 16A to 16N is operated by the SCA/-controller 23. The detector elements which are located within two ranges $\beta_1$ and $\beta_2$ ($\beta_1$ is equal to $\beta_2$) are coupled via the operated switching member 55 to the single channel analyzers 16A to 16N. This switching operation is the same as in the previous embodiment. In other words the detector signals can be derived only from the outer detector elements which are located at a certain instant within the ranges defined by two angles $\beta_1$ and $\beta_2$.

An electrical connection between the inner ring 94 and the input cables of the first analyzer unit 45 can be easily realized by the conventional slip ring mechanism.

In accordance with the arrangement shown in FIG. 6, the trails of the incident gamma rays can be inspected under the algorithm of the coincidence counting and the tomographic images of the radioisotope distribution can also be reconstructed.

The particular advantage of the third preferred embodiment is obtained in cases where many chance-coincidences occur and complicated circuitry is required in the electrical connection between the single channel analyzers and the inner/outer detector groups DI, DO.

In the foregoing embodiments, the energy levels of the detection, i.e., the single channel analyzers were preset to fixed values. However, it is of course possible to preset that the energy level widths of the channel analyzers have allowance or tolerance in their values. For instance, the energy level width of the first analyzer may be preset to 20 KeV±5 KeV and that of the second analyzer may be preset to 120 KeV±10 KeV. As a result, a more precise photon detection can be realized than in the fixed energy levels.

Generally, the gamma ray scatters within the object under examination, whereby it loses a little energy level, say ΔE'. This lost energy level ΔE' is considerably smaller than the above lost energy level ΔE. To improve capability of the detection, or analysis over the various energy levels of the incident gamma rays upon the detectors, it is preferable to preset the energy levels (threshold levels) of the first and second analyzers (i.e., single channel analyzers to, for example, a lower level than ΔE. This lower level can have also a predetermined range (width) for allowance, e.g., ±5 KeV. In other words, since the gamma ray, directly reaches the inner detector element, or firstly scatters in the object and is thereafter incident upon it, the preset energy level width (i.e., threshold level range of the analyzer) must cover both cases, i.e., a lower value than the known lost energy (ΔE) and a width, or tolerance (±5 KeV).

It should be noted that in the foregoing embodiments, a predetermined correlation is given to the inner and outer detector elements, i.e., the positional coincidence thereof along the radius, but it is possible to position, for instance, the outer detector elements at random on the outer ring.

While the preferred embodiments have been described, the ring type single-photon ECT imaging apparatus according to the present invention can provide the radioisotope distribution of the desirable slice under the higher time and spatial resolutions without using the conventional mechanical collimator, and further the dynamic scanning.

What is claimed is:

1. A single-photon emission computerized tomography imaging apparatus comprising:

first ring-shaped means including thereon a plurality of first detector elements and surrounding an object under examination to which radioisotope has been administered;

second ring-shaped means including thereon a plurality of second detector elements and concentrically surrounding the first ring-shaped means, wherein a gamma ray irradiated from the administered radioisotope through the object firstly scatters in one of the first detector elements, producing a first detector signal and thereafter the scattered gamma ray disappears in one of the second detector elements, producing a second detector signal;

first analyzing means including a plurality of first single channel analyzers coupled to the corresponding first detector elements for analyzing whether an energy level of the first detector signal is involved in a first predetermined level width of the first single channel analyzers and producing a first analyzing signal;

second analyzing means including a plurality of second single channel analyzers coupled to the corresponding second detector elements for analyzing whether an energy level of the second detector signal is involved in a second predetermined level width of the second single channel analyzers and producing a second analyzing signal;

image reconstruction means for reconstructing a computerized tomographic image signal by processing the first and second analyzing signals, said first and second analyzing signals containing both first data on the positional information of the first and second detector elements upon which said gamma ray and scattered gamma ray are incident, and second data on the energy information derived from the first and second analyzing means; and means for displaying a computerized tomographic image by receiving the reconstructed tomographic image signal.

2. An apparatus as claimed in claim 1, wherein said image reconstruction means includes:

a counting circuit for counting the number of the gamma-photon coincidence by receiving the first and second analyzing signals, and producing a counting signal;

a data processing circuit for processing the counting signal of the gamma-photon counting to derive the reconstructed tomographic image signal; and a controller for controlling at least first and second predetermined level widths of the first and second single channel analyzers, respectively.

3. An apparatus as claimed in claim 2, wherein said gamma-photon counting circuit includes:

a first selector/sample holder connected to the first single channel analyzers for selecting and holding said data on the positional information and the energy information of the first detector elements from the first detector signal and producing a start signal;

a second selector/sample holder connected to the second single channel analyzers for selecting and holding said data on the positional information and the energy information of the second detector elements from the second detector signal and producing a stop signal;

a time-to-amplitude converter connected to receive said start and stop signals for producing a single pulse having a peak value which corresponds to a duration time of operations thereof determined by the start and stop signals of the first and second selector/sample holders; and a third single channel analyzer connected to the time-to-amplitude converter for analyzing said single pulse to produce an enable signal based upon a third predetermined energy level width, wherein said enable signal enables the first and second selector holders to deliver said first and second data on the positional information to the image reconstruction means.

4. An apparatus as claimed in claim 2, wherein said data processing circuit includes:

an acquisition interface for temporarily acquiring both said first and second data on the positional information and the energy information derived from the first and second analyzing means;

a central processing unit for processing both said data on the positional and energy information to produce the reconstructed tomographic image signal; and a memory for temporarily storing the reconstructed tomographic image signal.

5. An apparatus as claimed in claim 2, wherein said first and second predetermined level widths of the first and second single channel analyzers are preset to be wider than said third predetermined level width of the third single channel analyzer.

6. An apparatus as claimed in claim 1, wherein said first and second ring-shaped means are fixed in a positional relationship to the object during the gamma-photon detection.

7. An apparatus as claimed in claim 1, wherein:

an emission shielding member having openings through which the gamma ray photons can pass is concentrically provided in front of a part of said inner detector elements along a gamma-photon path;

rotation controller means permits the emission shielding member to be rotated around the object;

a first switching member is interposed between the inner detector elements and the first single channel analyzers; and a second switching member is interposed between the outer detector elements and the second single channel analyzers, wherein switching operations of said first and second switching members are controlled in synchronism with the output of the rotation controller means, so that only said inner and outer detector elements receiving the gamma ray photons through said openings of the shielding member are electrically connected to the respective first and second single channel analyzers.

8. An apparatus as claimed in claim 1, wherein:

an emission shielding member having openings is mounted on the first ring means in such a manner that said first detector elements are positioned in said openings, wherein the gamma ray photons can pass through only said first detector elements located in the openings;

rotation controller means permits the first ring means to be rotated around the object;

a slip ring mechanism is interposed between the inner detector elements and the corresponding first single channel analyzers; and a switching member is interposed between the outer detector elements and the corresponding second single channel analyzers, wherein the switching operation of said switching member is controlled in synchronism with the output of the rotation controller means, so that only said outer detector elements receiving the gamma ray photons are electrically connected to the corresponding second single channel analyzers.

9. An apparatus as claimed in claim 1, wherein said first and second predetermined level widths of the first and second single channel analyzers are changed in accordance with the sort of administered radioisotope.

10. An apparatus as claimed in claim 1, wherein said first detector elements are made of a germanium semiconductor and said second detector elements are made of a combination of an NaI(sodium iodide) scintillator and a photomultiplier.

11. A single-photon emission computerized tomography imaging apparatus comprising:

first ring-shaped means including thereon a plurality of first detector elements and surrounding an object under examination to which radioisotope has been administered;

second ring-shaped means including thereon a plurality of second detector elements and concentrically surrounding the first ring-shaped means, wherein a gamma ray irradiated from the administered radioisotope through the object firstly scatters in one of the first detector elements, producing a first detector signal and thereafter the scattered gamma ray disappears in one of the second detector elements, producing a second detector signal;

first analyzing means including a plurality of first single channel analyzers coupled to the corresponding first detector elements for analyzing whether an energy level of the first detector signal is equal to a first predetermined level of the first single channel analyzers and producing a first analyzing signal;

second analyzing means including a plurality of second signal channel analyzers coupled to the corresponding second detector elements for analyzing whether an energy level of the second detector signal is equal to a second predetermined level of the second single channel analyzers and producing a second analyzing signal;

image reconstruction means for reconstructing a computerized tomographic image signal by processing the first and second analyzing signals, said first and second analyzing signals containing both first data on the positional information of the first and second detector elements upon which said gamma ray and scattered gamma ray are incident, and second data on the energy information derived from the first and second analyzing means; and means for displaying a computerized tomographic image by receiving the reconstructed tomographic image signal.

12. An apparatus as claimed in claim 11, wherein said image reconstruction means includes:

a counting circuit for counting the number of the gamma-photon coincidence by receiving the first and second analyzing signals and producing a counting signal;

a data processing circuit for processing the counting signal of the gamma-photon counting to derive the reconstructed tomographic image signal; and a controller for controlling at least first and second predetermined levels of the first and second single channel analyzers, respectively.

13. An apparatus as claimed in claim 12, wherein said gamma-photon counting circuit includes:

a first selector/sample holder connected to the first single channel analyzers for selecting and holding said data on the positional information and the energy information of the first detector elements from the first detector signal and producing a start signal;

a second selector/sample holder connected to the second single channel analyzers for selecting and holding said data on the positional information and the energy information of the second detector elements from the second detector signal and producing a stop signal;

a time-to-amplitude converter connected to receive said start and stop signals for producing a single pulse having a peak value which corresponds to a duration time of operations thereof determined by the start and stop signals of the first and second selector/sample holders;

a third single channel analyzer connected to the time-to-amplitude converter for analyzing said single pulse to produce an enable signal, based upon a third predetermined energy level, wherein said enable signal enables the first and second selector/sample holders to deliver said first and second data on the positional information to the image reconstruction means.

14. An apparatus as claimed in claim 12, wherein said data processing circuit includes:

an acquisition interface for temporarily acquiring both said first and second data on the positional information and the energy information derived from the first and second analyzing means;

a central processing unit for processing both said data on the positional and energy information to produce the reconstructed tomographic image signal; and a memory for temporarily storing the reconstructed tomographic image signal.

15. An apparatus as claimed in claim 12, wherein said first and second predetermined levels of the first and second single channel analyzers are different from said third predetermined level of the third single channel analyzer.

16. An apparatus as claimed in claim 11, wherein said first and second ring-shaped means are fixed in a positional relationship to the object during the gamma-photon detection.

17. An apparatus as claimed in claim 11, wherein:

an emission shielding member having openings through which the gamma ray photons can pass is concentrically provided in front of a part of said inner detector elements along a gamma-photon path;

rotation controller means permits the emission shielding member to be rotated around the object;

a first switching member is interposed between the inner detector elements and the first single channel analyzers; and a second switching member is interposed between the outer detector elements and the second single channel analyzers, wherein switching operations of said first and second switching members are controlled in synchronism with the output of the rotation controller means, means so that only said inner and outer detector elements receiving the gamma ray photons through said openings of the shielding member are electrically connected to the respective first and second single channel analyzers.

18. An apparatus as claimed in claim 11, wherein:

an emission shielding member having openings is mounted on the first ring means in such a manner that said first detector elements are positioned in said openings, wherein the gamma ray photons can pass through only said first detector elements located in the openings;

rotation controller means permits the first ring means to be rotated around the object;

a slip ring mechanism is interposed between the inner detector elements and the corresponding first single channel analyzers; and a switching member is interposed between the outer detector elements and the corresponding second single channel analyzers, wherein the switching operation of said switching member is controlled in synchronism with the output of the rotation controller means, so that only said outer detector elements receiving the gamma ray photons are electrically connected to the corresponding second single channel analyzers.

19. An apparatus as claimed in claim 11, wherein said first and second predetermined levels of the first and second single channel analyzers are changed in accordance with the sort of administered radioisotope.

20. An apparatus as claimed in claim 11, wherein said first detector elements are made of a germanium semiconductor and said second detector elements are made of a combination of an NaI(sodium iodide) scintillator and a photomultiplier.

* * * * *

UNITED STATES PATENT AND TRADEMARK OFFICE
CERTIFICATE OF CORRECTION

PATENT NO. : 4,639,599

DATED : January 27, 1987

INVENTOR(S) : TAKASHI ICHIHARA

It is certified that error appears in the above-identified patent and that said Letters Patent is hereby corrected as shown below:

Claim 17, line 13, delete "means" (second occurrence).

Signed and Sealed this

Twenty-fifth Day of August, 1987

Attest:

DONALD J. QUIGG

*Attesting Officer*  *Commissioner of Patents and Trademarks*